United States Patent [19]
Rachel et al.

[11] Patent Number: 5,096,812
[45] Date of Patent: Mar. 17, 1992

[54] ASSAY METHOD FOR GAMMA GLUTAMYLTRANSFERASE (GGT) IN LIQUID BLOOD AND DRIED BLOOD

[75] Inventors: Jane M. Rachel; Laura M. Smith, both of Kansas City, Mo.; Linda R. Pfaltzgraff, Osawatomie, Kans.

[73] Assignee: Osborn Laboratories, Inc., Shawnee Mission, Kans.

[21] Appl. No.: 363,216

[22] Filed: Jun. 8, 1989

[51] Int. Cl.$^5$ .......................... C12Q 1/48; C12Q 1/37
[52] U.S. Cl. .......................................... 435/15; 435/24
[58] Field of Search ........................ 435/15, 24, 805

[56] References Cited

U.S. PATENT DOCUMENTS

| | | | |
|---|---|---|---|
| 4,547,460 | 10/1985 | Eikenberry | 435/15 |
| 4,560,650 | 12/1985 | Bauer, III et al. | 435/15 |
| 4,603,107 | 7/1986 | Deneke et al. | 435/15 |
| 4,889,797 | 12/1989 | Amano et al. | 435/4 |

OTHER PUBLICATIONS

Filter Paper in Clinical Diagnostic Screening, Clinical Lab Products 11(10): 21–25, 1982; Kremer, R. D.
A Simple Phenylalanine Method for Detecting Phenylketonuria in Large Populations of Newborn Infants, Pediatrics 32(3): 338–343, 1963; Guthrie, R., Susa, A.
Mass Screening for Genetic Disease, Hospital Practice 7: 93–100, 1972; Guthrie, R.
Filter Paper Blood Collection and Punching as a Means of Quantification, Clin. Chem. 15(5): 381–389, 1969; Hill, J. B., Palmer, P.
A Kinetic Photometric Method for Serum Gamma Glutamyl Transpeptidase, Clin. Chem. 15(2): 124–136, 1969; Szasz, G.
Determination of Gamma Glutamyltransferase in Completely Haemolysed Blood Samples, Scand J. Clin Lab Invest 45: 661–664, 1985; Gjerde, H., Morland, J.
A Routine Procedure for Estimating Serum Gamma–Glytamyl-Transpeptidase Activity, Clin. Chim Acta 26:293–296, 1969; Whitaker, J. F., Tracey, D., Naftalin, L., Sexton, M.
Determination of Sulfanilamide in Blood and Urine, J. Biol. Chem. 122: 263–73, 1937–1938; Marshall, E. K.
A New Coupling Component for Sulfanilamide Determination, J. Biol. Chem. 128: 537–50, 1939; Bratton, A. C., Marshall, E. K.

*Primary Examiner*—David M. Naff
*Assistant Examiner*—Timothy J. Reardon
*Attorney, Agent, or Firm*—Richard P. Stitt

[57] ABSTRACT

A method of gamma glutamyltransferase (GGT) analysis is suitable for use with hemolyzed fluid or dried whole blood samples which avoids the need for protein precipitation or centrifugation of the sample. Analysis is by first mixing a fluid or dried whole blood sample with a phosphate buffered saline solution containing a nonionic biological detergent. The mixture is then vigorously agitated for one hour at room temperature. The activity of the GGT is then determined by reacting the mixture with a GGT substrate. Color is developed by a diazo coupling reaction with the enzyme reaction product. The intensity of the color is then measured.

16 Claims, No Drawings and a method to assay for gamma glutamyltransferase (GGT) activity in such whole blood samples. In particular, this invention provides an apparatus for transporting samples of dried whole blood, and a method for analysis of GGT in samples of dried or fluid whole blood which may exhibit partial or complete hemolysis.

ASSAY METHOD FOR GAMMA GLUTAMYLTRANSFERASE (GGT) IN LIQUID BLOOD AND DRIED BLOOD

FIELD OF THE INVENTION

This invention relates to improvements in an apparatus for transporting whole blood samples and a method to assay for gamma glutamyltransferase (GGT) activity in such whole blood samples. In particular, this invention provides an apparatus for transporting samples of dried whole blood, and a method for analysis of GGT in samples of dried or fluid whole blood which may exhibit partial or complete hemolysis.

BACKGROUND OF THE INVENTION

The enzyme gamma glutamyltransferase (GGT) catalyses the transfer of a gamma glutamyl moiety to an amino acid or peptide. The enzyme is present in the liver, kidney, prostate, pancreas, blood and other tissues. GGT is believed to be part of the glutathione cycle.

Elevation of the blood GGT level has been demonstrated to be an indicator of various diseases. Initially, the elevation of the blood GGT level, as measured by increased GGT activity in blood samples, was used as a test for diseases of the liver, bile ducts, and pancreas. It has since become commonly used as a general indicator of liver disorder. Increased blood GGT activity is indicative of liver dysfunction and may indicate pathology due to high alcohol consumption, drug use or disease. Elevated GGT activity has also been noted in conjunction with other diseases such as myocardial infarction, pancreatitis, and intra-cerebral tumors.

Currently, the amount of GGT present in blood is commonly measured using a kinetic assay on blood serum wherein (gamma-L-glutamyl)-p-nitroanilide and glycylglycine are the substrates for the GGT enzymatic formation of p-nitroaniline. The substrates are allowed to react with serum GGT for approximately 10 minutes. The p-nitroaniline produced in this reaction is then measured spectrophotometrically in the wavelength range of 405-410 nm. The rate of p-nitroaniline formation is proportional to GGT activity. Therefore, a high conversion to p-nitroaniline is indicative of a high GGT concentration in the serum, which may be due to liver degradation.

This method, however, is not applicable to analysis of blood samples in which the red blood cells have been ruptured or hemolysed. Any disruption of red blood cells prior to testing will interfere with an accurate determination of GGT activity, due to the strong light absorption by hemoglobin in the wavelength range used to observe the formation of p-nitroaniline. Methods of analysis have been developed to deal with the presence of hemoglobin in the sample. These methods involve post-reaction precipitation of blood protein by trichloroacetic acid followed by centrifugation of the sample. While this procedure avoids hemoglobin interference it retains the need for a large fluid blood sample volume that must be obtained from the subject and adds additional steps to the assay procedure.

An alternative to direct measurement of the p-nitroaniline is a method in which the GGT enzyme reaction product, p-nitroaniline, is diazotized and coupled with a chromophore to produce a mixture more suitable for spectrophotometric analysis. This method, however, utilizes blood serum and is not applicable to whole blood samples or samples of dried blood as is the method of the present invention.

Presently available assay methods which utilize fluid blood serum samples for determination of GGT activity are ineffective when blood sample damage has occurred during shipping. Sample damage may result in hemolysis or enzyme denaturation with subsequent enzyme activity loss. In addition, leaking fluid sample packages create a potential health hazard for personnel who are required to handle packages containing fluid blood, physiological fluids, or chemical reagents.

Analysis of GGT activity in blood is being employed by insurers to determine the desirability of offering insurance contracts to potential customers. This use is increasing the submission of physiological fluid samples, such as blood or urine, to laboratories from persons residing far from the laboratory. The advent of such distant sampling presents a number of problems in assaying for GGT activity. Conveyance of these samples to the laboratory often occurs under poor conditions. Mistreatment of blood samples and concomitant rupture of red blood cells introduces hemoglobin into the sample resulting in interference with the current GGT assay procedures. The use of public and private mail delivery systems to transport such samples increases the potential for careless handling. Damaged and leaking fluid samples may alarm or endanger mail system workers who contact the damaged and leaking packages of blood or other fluid physiological materials. Finally, mishandling of blood samples may cause a loss of GGT activity due to denaturation of the GGT enzyme and result in unreliable test results.

OBJECTS OF THE INVENTION

It is, therefore, an important object of the present invention to provide a method and apparatus to obtain GGT and to assay for GGT activity in whole blood which is independent of fluid sample collection techniques and the problems of sample container integrity and fluid sample damage presented by transporting fluid blood samples.

Another important object of the present invention is to provide a method of assaying for GGT activity in whole blood which does not require prior separation of the blood serum or precipitation of the blood proteins and is unaffected by the presence of hemolytic contaminants in the test sample.

Furthermore, it is an important objective of this invention to provide a method and apparatus to obtain and assay for GGT activity which can utilize a convenient and stable sample means to convey the blood sample to the laboratory and thereby avoid the previous fluid sample transportation difficulties while providing greater protection for transportation employees and laboratory personnel from potentially harmful components associated with fluid biological samples of unknown origin.

Other objects and advantages of this invention will become apparent from the following description, wherein is set forth by way of illustration and example, an embodiment of this invention.

DESCRIPTION OF THE PREFERRED EMBODIMENT

The present invention is adapted to utilizing a sample of fluid or dried or partially dried whole blood from which is obtained GGT. The GGT is obtained in a manner which retains substantial enzyme activity. In using dried blood as the source for GGT, the problems of leaking packages endangering personnel as well as blood sample damage resulting from careless handling by transport workers are avoided. As separation of the blood serum is not required for operation of the inventive method, small quantities of fluid whole blood may act as the source for GGT. The sample volume of blood required for transport may be so substantially reduced as to avoid the dangers presented by shipment of the relatively large volumes of fluid blood required in GGT assays which involve separation of the blood serum prior to testing.

The method of analysis of GGT activity contained herein also avoids the interference previously presented by the presence of hemoglobin in the blood sample and thus reduces the need for careful handling of the sample during transportation to the laboratory.

One embodiment of the invention utilizes a whole blood specimen which is applied to an absorbent support means. The absorbent support means may be such that the blood sample may either adhere to the surfaces of the support means, or alternatively be taken into the body of the support means. By way of example, and not limitation, blood may be absorbed onto the surface of a sheet of glass. Alternatively, blood may be absorbed into a cotton pad or absorbed into a volume of diatomaceous earth.

A predetermined quantity of blood may be applied to the absorbent support means or the absorbent support means may be such that it will absorb a known quantity of blood either by volume, weight, or surface area of the absorbent support means. Alternatively, an unmeasured amount of blood may be applied to the absorbent support means for later quantification. Examples of acceptable absorbent support means are cellulose fiber such as paper or cotton fiber, or glass, fritted glass, or diatomaceous earth, with a cellulose fiber such as paper being the preferred embodiment. Other well-known absorbent means are equally satisfactory as a structure to hold the blood sample.

The blood sample so applied to the absorbent support means is then dried while remaining in contact with the absorbent support means. The assay method of the invention may be used with such dried blood samples even though the manner of sample collection or subsequent drying or transportation has resulted in complete hemolysis of the blood sample.

After absorption and drying of the blood sample, a dried blood hemolysate is prepared by adding a quantity of the dried blood sample to a solubilizing means and the resultant mixture may then be vigorously agitated to aid solubilization. The dried blood may be either first separated from the absorbent means or left in contact with the absorbent means during solubilization. The solubilizing means may be a volume of water or saline solution and may include a buffer system to maintain a substantially constant pH. A quantity of a non-ionic biological detergent may also be added to the solubilizing means to facilitate solubilization. The quantity of the solubilizing means combined with the dried blood is sufficient so as to result in a maximum dilution of the original fluid blood sample volume to a ratio of about 1:60. The buffer system may be selected from phosphoric, citric, formic, boric, acetic, and succinic acids or any available and convenient buffer system that would provide a substantially constant pH and non-absorbance in the wavelength range selected for the colorimetric determination. Examples of non-ionic detergents which may be used in the above methods are octylphenol-ethylene oxide (Nonidet P-40 ®), polyoxyethylene ethers (BRIJ ®), polyoxyethylenesorbitan (TWEEN ®), sorbitan (SPAN ®), or Triton X-100 ® (octylphenylpoly [ethylene glycol ether]$_n$).

A volume of the dried blood hemolysate is then added to an approximately ten fold greater volume of a GGT substrate such as (gamma-L-glutamyl)-p-nitroanilide. This mixture is then allowed to react for a time greater than one-half hour. The reaction time may be as short as one-half hour or allowed to continue overnight, however, a reaction time of two hours is optimal for the development of color in samples exhibiting low enzyme activity. Room temperature is compatible with consistent results. If the reaction is to continue for many hours a reduction in the temperature to a range of 2°-8° C. is preferable. The optimal reaction temperature is approximately 37° centigrade.

Upon termination of the reaction period, color development in the sample is achieved by addition of a volume of an aqueous acid such as phosphoric acid, citric acid, formic acid, boric acid, succinic acid, hydrochloric acid or acetic acid. Addition of the acid is followed by a volume of a nitrite source; and volume of an acceptor for excess nitrite. Next is added and a volume of a diazo coupling means to form the diazo derivative of the GGT enzyme reaction product in the mixture. Examples of satisfactory diazo coupling reagents are N-(1-naphthyl) ethyleneamine, 1-amine-5-Naphthol, 2-amino-5-Naphthol, and 1-amino-8-Naphthol. Color in the test sample develops rapidly and a spectrophotometric reading may then be obtained in the wavelength range of 475 nm to 600 nm.

In one example of this preferred embodiment the whole blood was applied to thick absorbent paper and allowed to dry. A disk, one-quarter inch in diameter, was then punched from the paper. The dried blood hemolysate was then prepared by soaking the disk in 0.100 ml of phosphate-buffered saline of pH 7.4, containing 0.5% Triton X-100 ®, at room temperature for one hour with vigorous agitation. A 0.025 ml volume of the hemolysate was then added to 0.250 ml of a saturated solution of (gamma-L-glutamyl)-p-nitroanilide in 0.1 M TRIS ® [(hydroxymethyl) aminomethane hydrochloride] at pH 8.2 and made in 0.1 M glycylglycine. This solution was incubated for 120 minutes at 37° centigrade. At the conclusion of the reaction period, 1.0 ml of 10% acetic acid, 0.5 ml of 0.1% sodium nitrite, 0.5 ml of 0.5% ammonium sulfamate, and 0.5 ml of 0.1% N-(1-naphthyl) ethylenediamine dihydrochloride were added to the reaction mixture to diazotize the enzyme reaction end-product p-nitroaniline. The color intensity of the resulting diazo compound chromophore was observed at wavelength 540 nm. The degree of color intensity was proportional to the degree of GGT activity in the sample.

In a second example of the preferred embodiment a fluid blood sample was applied to the interior walls of a glass vial and allowed to dry upon the walls and interior base of the glass vial. The dried blood hemolysate was then prepared by adding to the vial 0.200 ml of water and allowing the blood to dissolve in the water without agitation. A 0.025 ml volume of the hemolysate was then added to 0.250 ml of a saturated solution of (gamma-L-glutamyl)-p-nitroanilide in 0.1 M TRIS ® [(hydroxymethyl) aminomethane hydrochloride] at pH 8.2 and made in 0.1 M glycylglycine. This solution was incubated overnight at room temperature. At the conclusion of the reaction, 1.0 ml of 1 N hydrochloric acid, 0.5 ml of 0.1% potassium nitrite, 0.5 ml of 0.5% ammonium sulfamate, and 0.5 ml of 0.1% N-(1-naphthyl) ethylenediamine dihydrochloride were added to the reaction mixture to create the diazo derivative of the enzyme reaction end-product. The color intensity of the resulting diazo compound chromophore was then measured at wavelength 575 nm. The degree of absorption was proportional to the degree of GGT activity in the sample.

In a third example of the preferred embodiment a known volume of blood was added to a small quantity of diatomaceous earth and allowed to dry. The dried blood hemolysate was then prepared by the addition of 0.200 ml of saline of pH 6.0 with agitation. A 0.025 ml volume of the hemolysate was added to 0.250 ml of a 0.007 molar solution of (gamma-L-glutamyl)-3-carboxy-p-nitroanilide in 0.1 M TRIS ® [(hydroxymethyl) aminomethane hydrochloride] at pH 8.2 and made in 0.1 M glycylglycine. This solution was incubated for one hour at 37° centigrade. At the conclusion of the reaction, 1.0 ml of 1 N hydrochloric acid, 0.5 ml of 0.1% sodium nitrite, 0.5 ml of 0.5% sulfamic acid, and 0.5 ml of 0.05% N-(1-naphthyl) ethylenediamine dihydrochloride were added to the reaction mixture to diazotize the enzyme reaction end-product. The color intensity of the resulting diazo compound chromophore was then observed at wavelength 500 nm. The degree of absorption was proportional to the degree of GGT activity in the sample.

An alternative embodiment of the invention utilizes small volumes of whole blood in either fluid form or partially dehydrated form. In one example of this preferred embodiment whole blood was added to 0.250 ml of a saturated solution of (gamma-L-glutamyl)-p-nitroanilide in 0.1 M TRIS ® [(hydroxymethyl) aminomethane hydrochloride] at pH 8.2 and made in 0.1 M glycylglycine. This solution was incubated for 120 minutes at 37° centigrade. At the conclusion of the reaction period, 1.0 ml of 10% acetic acid, 0.5 ml of 0.1% sodium nitrite, 0.5 ml of 0.5% ammonium sulfamate, and 0.5 ml of 0.1% N-(1-naphthyl) ethylenediamine dihydrochloride were added to the reaction mixture to diazotize the enzyme reaction end-product p-nitroaniline. The color intensity of the resulting diazo compound chromophore was observed at wavelength 540 nm. The degree of color intensity was proportional to the degree of GGT activity in the sample.

In a second example of this alternative embodiment a fluid whole blood sample was added to 0.250 ml of a saturated solution of (gamma-L-glutamyl)-p-nitroanilide in 0.1 M TRIS ® [(hydroxymethyl) aminomethane hydrochloride] at pH 8.2 and made in 0.1 M glycylglycine. This solution was incubated for 90 minutes at 37° centigrade. At the conclusion of the reaction, 1.0 ml of 1 N hydrochloric acid, 0.5 ml of 0.1% potassium nitrite, 0.5 ml of 0.5% ammonium sulfamate, and 0.5 ml of 0.1% N-(1-naphthyl) ethylenediamine dihydrochloride were added to the reaction mixture to create the diazo derivative of the enzyme reaction end-product. The color intensity of the resulting diazo compound chromophore was then measured at wavelength 575 nm. The degree of absorption was proportional to the degree of GGT activity in the sample.

In a third example of this alternative embodiment fluid whole blood was added to 0.250 ml of a 0.007 molar solution of (gamma-L-glutamyl)-3-carboxy-p-nitroanilide in 0.1 M TRIS ®[(hydroxymethyl) aminomethane hydrochloride] at pH 8.2 and made in 0.1 M glycylglycine. This solution was incubated for one hour at 37° centigrade. At the conclusion of the reaction, 1.0 ml of 1N hydrochloric acid, 0.5 ml of 0.1% sodium nitrite, 0.5 ml of 0.5% sulfamic acid, and 0.5 ml of 0.05% N-(1-naphthyl) ethylenediamine dihydrochloride were added to the reaction mixture to diazotize the enzyme reaction end-product. The color intensity of the resulting diazo compound chromophore was then observed at wavelength 500 nm. The degree of absorption was proportional to the degree of GGT activity in the sample.

It is to be understood that while certain forms of this invention have been illustrated and described, it is not limited thereto, except insofar as such limitations are included in the following claims.

Having thus described the invention, what is claimed as new and desired to be secured by Letters Patent is:

1. A method of assaying the activity of gamma glutamyltransferase (GGT) obtained from a blood sample which comprises:
   applying a fluid, whole blood sample or fluid, hemolytic blood sample to a means for absorbent support;
   drying the blood sample on the means for absorbent support to produce a dried blood sample;
   dissolving the GGT contained in the dried blood sample by combining a quantity of the dried blood sample with a means for solubilizing the dried blood sample to produce a first mixture such that the maximum dilution of the fluid blood sample volume in the solubilizing means is about 1:60;
   reacting for a time in excess of one-half hour a portion of the first mixture with a gamma glutamyltarnsferase substrate and a gamma glutamyl acceptor to produce a second mixture;
   adding to the second mixture aqueous solutions of an acid, a nitrite source, a means for accepting excess nitrile, and a means for diazo coupling, in sufficient relative quantities to produce a colored final mixture; and
   measuring the color intensity of the final mixture at a wavelength in the range of 475 to 600 nanometers, said color intensity being proportional to enzyme activity.

2. The method of claim 1 wherein the means of absorbent support is selected from the group consisting of cellulose fiber, glass, fritted glass, cotton fiber, paper, and diatomaceous earth.

3. The method of claim 1 wherein the means for solubilizing is selected from the group consisting of water, saline, buffered saline, and buffered water.

4. The method of claim 1 wherein the means for solubilizing includes a non-ionic detergent.

5. The method of claim 1 wherein the first mixture is agitated or sonicated.

6. The method of claim 1 wherein the acid is selected from the group consisting of phosphoric, citric, formic, boric, succinic, hydrochloric and acetic acids.

7. The method of claim 1 wherein the nitrite source is selected from the group consisting of sodium nitrite and potassium nitrite.

8. The method of claim 1 wherein the gamma glutamyltransferase substrate is selected from the group consisting of (gamma-L-glutamyl)-p-nitroanilide, and (gamma-L-glutamyl)-3-carboxy-p-nitroanilide.

9. The method of claim 1 wherein the means for accepting excess nitrite is selected from the group consisting of ammonium sulfamate and sulfamic acid.

10. The method of claim 1 wherein the means for diazo coupling is selected from the group consisting of N-(1-naphthyl) ethylenediamine dihydrochloride, 1-Naphthylamine, 2-Naphthylamine, 1-amino-5-Naphthol, 2-amino-5-Naphthol, and 1-amino-8-Naphthol.

11. A method of assaying the activity of gamma glutamyltransferase in a sample of whole blood which comprises:

reacting for a time in excess of one-half hour whole blood with a gamma glutamyltransferase substrate and a gamma glutamyl acceptor to produce a mixture;

adding to the mixture aqueous solutions of an acid, a nitrile source, a means for accepting excess nitrile, and a means for diazo coupling, in sufficient relative quantities to produce a colored final mixture; and measuring the color intensity of the final mixture at a wavelength in the range of 475 to 600 nanometers, said color intensity being proportional to enzyme activity.

12. The method of claim 11 wherein the gamma glutamyltransferase substrate is selected from the group consisting of (gamma-L-glutamyl)-p-nitroanilide, and (gamma-L-glutamyl)-3-carboxy-p-nitroanilide.

13. The method of claim 11 wherein the acid is selected from the group consisting of phosphoric, citric, formic, succinic, hydrochloric and acetic acid.

14. The method of claim 11 wherein the nitrile source is selected from the group consisting of sodium nitrile and potassium nitrile.

15. The method of claim 11 wherein the means for accepting excess nitrile is selected from the group consisting of ammonium sulfamate and sulfamic acid.

16. The method of claim 11 wherein the means for diazo coupling is selected from the group consisting of N-(1-naphthyl) ethylenediamine dihydrochloride, 1-Naphthylamine, 2-Naphthylamine, 1-amino-5-Naphthol, 2-amino-5-Naphthol, and 1-amino-8-Naphthol.

* * * * *

UNITED STATES PATENT AND TRADEMARK OFFICE
CERTIFICATE OF CORRECTION

PATENT NO. : 5,096,812

DATED : March 17, 1992

INVENTOR(S) : Jane M. Rachel, Laura M. Smith and Linda R. Pfaltzgraff

It is certified that error appears in the above-identified patent and that said Letters Patent is hereby corrected as shown below:

```
Column 4, line 26, delete "and".
Column 4, line 30, delete "ethyleneamine" and substitute
    --ethylenediamine--.
Column 4, line 30, after "ethylenediamine," insert
    --dihydrochloride, 1-Naphthylamine, 2-Naphthylamine,--.
Column 4, line 30, delete "1-amine-5-Naphthol" and substitute
    --1-amino-5-Naphthol--.
Column 4, line 46, delete "in" and after "0.01 M" insert --in--.
Column 4, line 68, delete "in" and after "0.01 M" insert --in--.
Column 5, line 20, delete "in" and after "0.01 M" insert --in--.
Column 5, line 38, delete "in" and after "0.01 M" insert --in--.
Column 5, line 54, delete "in" and after "0.01 M" insert --in--.
Column 6, line 2, delete "in" and after "0.01 M" insert --in--.
Claim 1, column 6, line 24, after "hemolytic" delete "blood".
Claim 1, column 6, line 36, delete "glutamyltarnsferase" and
    substitute --glutamyltransferase--.
```

UNITED STATES PATENT AND TRADEMARK OFFICE
CERTIFICATE OF CORRECTION

PATENT NO. : 5,096,812

DATED : March 17, 1992

INVENTOR(S) : Jane M. Rachel, Laura M. Smith and Linda R. Pfaltzgraff.

It is certified that error appears in the above-identified patent and that said Letters Patent is hereby corrected as shown below:

Claim 1, column 6, line 40, delete "nitrile" and substitute --nitrite--.

Claim 2, column 6, line 47, delete the second occurrence of "of" and substitute --for--.

Claim 11, column 7, line 16, delete both occurrences of "nitrile" and substitute in both occurrences --nitrite--.

Claim 14, column 8, line 10, delete "nitrile" and substitute --nitrite--.

Claim 14, column 8, line 11, delete "nitrile" and substitute --nitrite--.

Claim 15, column 8, line 14, delete "nitrile" and substitute --nitrite--.

Signed and Sealed this

Twenty-third Day of June, 1992

Attest:

DOUGLAS B. COMER

*Attesting Officer*     *Acting Commissioner of Patents and Trademarks*